United States Patent [19]

Klaveness

[11] Patent Number: 5,322,681
[45] Date of Patent: Jun. 21, 1994

[54] CHELATING COMPOUNDS

[75] Inventor: Jo Klaveness, Oslo, Norway

[73] Assignee: Nycomed Imaging AS, Oslo, Norway

[21] Appl. No.: 910,318

[22] Filed: Jul. 17 1992

[30] Foreign Application Priority Data

Jan. 19, 1990 [GB] United Kingdom ................ 9001246
Apr. 9, 1990 [GB] United Kingdom ................ 9007984

[51] Int. Cl.$^5$ ................ A61K 49/00; C07F 15/02; C07D 498/08
[52] U.S. Cl. ................ 424/9; 534/15; 534/16; 540/465; 540/472
[58] Field of Search ........ 544/2, 5, 7, 65, 66, 544/181, 214, 215, 4, 10, 64; 424/9, 4.9; 540/541, 544, 552, 568, 465, 472, 467, 468, 489, 470, 471, 473, 474; 514/185, 299, 81, 247, 230.5, 223.8, 246, 186, 213, 221, 211; 534/15, 16; 549/10, 11, 352, 353

[56] References Cited

U.S. PATENT DOCUMENTS

| | | | |
|---|---|---|---|
| 2,387,976 | 9/1945 | Bersworth | 562/565 |
| 2,407,645 | 9/1946 | Bersworth | 562/565 |
| 2,751,390 | 6/1956 | Bersworth | 546/15 |
| 4,678,667 | 7/1987 | Meares et al. | 424/9 |
| 4,880,008 | 11/1989 | Lauffer | 424/9 |
| 4,957,939 | 9/1990 | Gries et al. | 424/4 |

FOREIGN PATENT DOCUMENTS

| | | |
|---|---|---|
| 71564 | 7/1982 | European Pat. Off. ........ 424/9 |
| 296522 | 12/1988 | European Pat. Off. . |
| 0299795 | 1/1989 | European Pat. Off. . |
| 326226 | 8/1989 | European Pat. Off. . |
| 327365 | 8/1989 | European Pat. Off. . |
| 352218 | 1/1990 | European Pat. Off. . |
| 3401052 | 7/1984 | Fed. Rep. of Germany ........ 424/9 |
| WO86/06605 | 11/1986 | World Int. Prop. O. . |
| WO89/11868 | 12/1989 | World Int. Prop. O. . |
| 8911868 | 12/1989 | World Int. Prop. O. . |
| 9011282 | 10/1990 | World Int. Prop. O. . |

OTHER PUBLICATIONS

Stetter et al. Tetrahedron Letters vol. 37 pp. 767–772, 1981.
Kodama J. Chem. Soc. Dalton Trans. 1980 pp. 327–333.
Lacoste et al., *J. Am. Chem. Soc.* 87, 2385–2388, 1965.
Alcock et al., *J. Chem. Soc. Dalton Trans.*, 2959–2963, 1988.
Alcock et al., *J. Chem. Soc., Chem. Commun.*, 1058–1059, 1985.
Hancock et al., *J. Am. Chem. Soc.*, 110, 2788–2794, 1988.
Ramasubbu et al., *J. Chem. Soc., Chem. Commun.*, 277–278, 1982.
Barefield et al., in Inorg. Chem., 25, 552–558, 1986.
Sabbatini et al., *J. Phys. Chem.*, 91, 4681–4685, 1987.
Smith et al., *J. Am. Chem. Soc.*, 111, 7437–7443, 1989.
Dhont et al., *Bull. Soc. Chim. Belg.*, 98(8), 575–576, 1989.
Hosseini et al., *Helvetica Chimica Acta*, 72, 1066–1077, 1989.
Wagnon et al., *Inorg. Chem.*, 28, 1923–1927, 1989.

*Primary Examiner*—John M. Ford
*Assistant Examiner*—P. K. Sripada
*Attorney, Agent, or Firm*—Bacon & Thomas

[57] ABSTRACT

The invention provides novel condensed macrocyclic chelants of formula $[X(CR^2R^3)_n]_m$, (wherein each X independently represents an oxygen or sulphur atom or a group of formula NH, $N(CR^2R^3)_pR^4$, $N(CR^2R^3)_pY$, or $N(CR^2R^3)_n-N((CR^2R^3)_pY)_2$; each Y independently represents a group COZ, $SO_2Z$, $POZ_2$, $CON(OH)R^2$, $CH_2SR^2$, $CS_2R^2$ or CSZ; each Z independently represents a group $OR^2$ or $NR^2R^2$; n is an integer of 1 to 4; m is an integer of 3 to 8; p is an integer of 1 to 3; each $R^2$ independently represents a hydrogen atom or a $C_{1-8}$ alkyl group optionally mono- or poly-substituted by hydroxyl or $C_{1-8}$ alkoxy groups and at least one pair of $R^2$ groups, in each pair one being from a $(CR^2R^3)_n$ moiety and the other being from a $(CR^2R^3)_n$ or $(CR^2R^3)_p$ moiety, together with the intervening atoms represents a 5 to 8 membered, saturated fused ring optionally containing one or more ring heteroatoms selected from nitrogen, oxygen and sulphur, said fused ring optionally being substituted by a group $R^1$; each $R^1$ independently represents a group $R^4$ or a nitrogen-attached group $(CR^2R^3)_pY$; each $R^3$ independently represents a hydrogen atom or a $C_{1-8}$ alkyl or $C_{1-8}$ alkoxy group optionally mono or poly substituted by hydroxy or $C_{1-8}$ alkoxy groups; and each $R^4$ independently represents a hydrogen atom, a halogen atom or a hydroxyl group or an optionally mono- or poly-hydroxylated $C_{1-8}$ alkyl, $C_{1-8}$ alkoxy, $(C_{1-8}$ alkoxy)-$C_{1-8}$ alkyl or poly-$(C_{1-8}$ alkoxy)-$C_{1-8}$ alkyl group, a sulphonate group or a group $(CR^2R^3)_pY$; with the proviso that at least 2 Y groups are present). These chelants are useful in the preparation of diagnostic and therapeutic agents, in particular chelate complexes suitable for use as contrast agents for diagnostic imaging techniques, e.g. MRI.

9 Claims, No Drawings

CHELATING COMPOUNDS

CHELATING COMPOUNDS

The present invention relates to certain novel chelating agents, in particular polyamines, and to their uses, especially their medical uses.

The medical use of chelating agents is well established, for example as stabilizers for pharmaceutical preparations, as antidotes for poisonous heavy metal species and as diagnostic agents for the administration of metal species (e.g. ions or atoms) for diagnostic techniques such as X-ray, magnetic resonance imaging (MRI) or ultrasound imaging or scintigraphy.

Polyamine chelating agents, for example aminopoly-(carboxylic acid or carboxylic acid derivative) (hereinafter APCA) chelating agents and their metal chelates, are well known and are described for example in U.S. Pat. No. 2,407,645 (Bersworth), U.S. Pat. No. 2,387,735 (Bersworth), EP-A-71564 (Schering), EP-A-130934 (Schering), EP-A-165728 (Nycomed AS), DE-A-2918842 (Rexolin Chemicals AB), DE-A-3401052 (Schering), EP-A-258616 (Salutar), DE-A-3633245 (Schering), EP-A-263059 (Schering), EP-A-277088 (Schering) and DE-A-3633243 (IDF).

Thus, for example, EP-A-71564 describes paramagnetic metal chelates, for which the chelating agents are nitrilotriacetic acid (NTA), N,N,N',N'-ethylenediamine-tetraacetic acid (EDTA), N-hydroxyethyl-N,N',N'-ethylenediamine-triacetic acid (HEDTA), N,N,N',N'',N''-diethylenetriamine-pentaacetic acid (DTPA) and N-hydroxyethylimino-diacetic acid, as being suitable as contrast agents for MRI, contrast being achieved by the effect of the magnetic field of the paramagnetic species (e.g. Gd(III)) with the chelating agents serving to reduce the toxicity and to assist administration of that paramagnetic species. Amongst the particular metal chelates disclosed by EP-A-71564 was Gd DTPA, the use of which as an MRI contrast agent has recently received much attention. The Gd(III) chelate of 1,4,7,10-tetraazacyclododecanetetra-acetic acid (DOTA), referred to in DE-A-3401052 (Schering) and in U.S. Pat. No. 4,639,365 (University of Texas), has also recently received attention in this regard.

To improve stability, water solubility and selectivity, relative to the APCA chelating agents described in EP-A-71564, Schering, in EP-A-130934, have proposed the partial substitution for the N-attached carboxyalkyl groups of alkyl, alkoxyalkyl, alkoxycarbonylalkyl or alkylaminocarbonylalkyl groups, where any amide nitrogens may themselves carry polyhydroxyalkyl groups. More recently, to improve compatibility, stability, solubility and selectivity, in EP-A-250358 Schering have proposed a narrow range of compounds having a DTPA-like structure including a bridging alkylene chain. In the field of hepatobiliary MRI contrast agents, where lipophilicity rather than hydrophilicity is desired, Nycomed in EP-A-165728, have proposed the use of paramagnetic chelates of certain anilide group-containing iminodiacetic acids and Lauffer in WO-A-86/06605 has suggested the use of paramagnetic chelates of triaza and tetraaza macrocycles which carry a fused aromatic ring but are otherwise unsubstituted.

Nycomed, in EP-A-299795, suggest that the toxicity of certain APCA chelating agents and their chelates may be reduced by introducing at least one hydrophilic moiety as a substituent on one or more of the alkylene bridges between the amine nitrogens.

However, all hitherto known APCA chelating agents and their metal chelates encounter problems of toxicity, stability or selectivity and there is thus a general and continuing need for such polyamine chelating agents which form metal chelates of reduced toxicity, improved stability or improved water solubility.

We now propose a novel class of polyamine chelating agents which incorporate within their structure a heterocyclic ring.

Thus viewed from one aspect the present invention provides a compound of formula I

wherein
each X independently represents an oxygen or sulphur atom or a group of formula NH, $N(CR^2R^3)_pR^4$, $N(CR^2R^3)_pY$, or $N(CR^2R^3)_n-N((CR^2R^3)_pY)_2$;
each Y independently represents a group COZ, $SO_2Z$, $POZ_2$, $COH(OH)R^2$, $CH_2SR^2$, $CS_2R^2$ or CSZ;
each Z independently represents a group $OR^2$ or $NR^2R^2$;
n is an integer of 1 to 4, preferably 2 or 3;
m is an integer of 3 to 8, preferably 3 to 6;
p is an integer of 1 to 3, preferably 1;
each $R^2$ independently represents a hydrogen atom or a $C_{1-8}$ alkyl group optionally mono- or poly-substituted by hydroxyl or $C_{1-8}$ alkoxy groups and at least one pair of $R^2$ groups, in each pair one being from a $(CR^2R^3)_n$ moiety and the other being from a $(CR^2R^3)_n$ or $(CR^2R^3)_p$ moiety (particularly preferably $R^2$ groups in $(CR^2R^3)_n$ and $(CR^2R^3)_p$ or $(CR^2R^3)_n$ and $(CR^2R^3)_n$ groups bonded to the same X group), together with the intervening atoms represents a 5 to 8 membered, preferably 5 or 6 membered, saturated fused ring optionally containing one or more, especially 1 or 2 ring heteroatoms selected from nitrogen, oxygen and sulphur, said fused ring optionally being substituted by a group $R^1$; each $R^1$ independently represents a group $R^4$ or a nitrogen-attached group $(CR^2R^3)_pY$;
each $R^3$ independently represents a hydrogen atom or a $C_{1-8}$ alkyl or $C_{1-8}$ alkoxy group optionally mono or poly substituted by hydroxy or $C_{1-8}$ alkoxy groups; and each $R^4$ independently represents a hydrogen atom, a halogen atom or a hydroxyl group or an optionally mono-or poly-hydroxylated $C_{1-8}$ alkyl, $C_{1-8}$ alkoxy, $(C_{1-8}$ alkoxy$)$-$C_{1-8}$ alkyl or poly-$(C_{1-8}$ alkoxy$)$-$C_{1-8}$ alkyl group, a sulphonate group or a group $(CR^2R^3)_pY$; with the proviso that at least 2 Y groups, preferably at least 3, are present) or a chelate complex or salt thereof.

In the compounds of the invention, alkyl or alkylene moieties in groups $R^1$ to $R^4$, unless otherwise stated, may be straight chained or branched and preferably contain from 1 to 8, especially preferably 1 to 6 and most preferably 1 to 4, carbon atoms. Where substituents may themselves optionally be substituted by hydroxyl or alkoxy groups, this may be monosubstitution or polysubstitution and, in the case of polysubstitution, alkoxy or hydroxyl substituents may be carried by alkoxy substituents.

Where, as is particularly preferred, the compounds of the invention incorporate one or more hydrophilic $R^1$ to $R^4$ groups, these are preferably straight-chained or branched moieties having a carbon atom content of from 1 to 8, especially preferably 1 to 6, carbon atoms. The hydrophilic groups may be alkoxy, polyalkoxy, hydroxyalkoxy, hydroxypolyalkoxy, polyhydroxyalkoxy, polyhydroxylated polyalkoxy, hydroxyalkyl, polyhydroxyalkyl, alkoxyalkyl, polyalkoxyalkyl, hydroxylated alkoxyalkyl, polyhydroxylated alkoxyalkyl, hydroxylated polyalkoxyalkyl, or polyhydroxylated polyalkoxyalkyl groups. More preferably however they will be monohydroxyalkyl or polyhydroxyalkyl groups. The hydrophilic groups serve to increase the hydrophilicity and reduce the lipophilicity of the metal chelates formed with the chelating agents of the invention and it is preferred that the compounds of formula I should contain at least 1, conveniently from 1 to 4, and preferably 1, 2 or 3 such hydrophilic groups. As hydrophilic groups, e.g. $R^1$ to $R^4$ and $(CR^2R^3)_pR^4$, the compounds of the invention may thus include for example hydroxymethyl, 2-hydroxyethyl, 2-hydroxypropyl, 1,2-dihydroxyethyl, 3-hydroxypropyl, 2,3-dihydroxypropyl, 2,3,4-trihydroxybutyl, 1-(hydroxymethyl)-2-hydroxyethyl, methoxymethyl, ethoxymethyl, 2-hydroxyethoxymethyl, methoxyethoxymethyl, (2-hydroxy-ethoxy)ethyl, etc, groups.

In the compounds of the invention, where two $R^2$ groups together with the intervening atoms form a fused cyclic group these fused groups preferably are cyclopentane, cyclohexane, oxolane, oxane, thiolane, thiane, pyrrolidine, piperidine, piperazine, morpholine or perhydropyrimidine. (It will be appreciated that where the two $R^2$ groups are not from the same $(CR^2R^3)_n$ group the fused ring will be heterocyclic).

N-membered fused rings attached to the macrocyclic skeleton of the molecule at, or at positions adjacent a ring heteroatom of the macrocycle and rings attached at the 1 and 2 or 2 and $N-1$ positions of the fused ring are especially preferred. Moreover, in the compounds according to the invention containing two or more fused rings, these are preferably separated by at least one and especially at least two X groups. Particularly preferably, where there are two or more fused rings, these will be spaced approximately uniformly about the macrocyclic skeleton.

It is also especially preferred that groups X comprising no ionizing group Y should be non-adjacent and particularly that they should adopt opposed positions in macrocyclic chelants, e.g. as the 1st and 3rd X groups in an 6 X ring. Particularly preferably such groups are hydrophilic groups such as are defined above.

Particularly preferred compounds of formula I include those of formula Ib

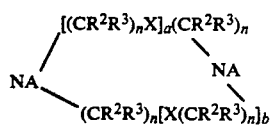 (Ib)

where
a and b are each zero, 1, 2 or 3, the sum of a and b being 1 to 3; d is 2,3 or 4;
n is as hereinbefore defined but preferably 2 or 3;
A is hydrogen or optionally hydroxylated, optionally alkoxylated alkyl or $CHR^2Y$;
$R^3$ is hydrogen or optionally hydroxylated alkyl;

$R^2$ is hydrogen or optionally hydroxylated, optionally alkoxylated alkyl and at least one pair of $R^2$ groups together with the intervening atoms form a fused ring of formula

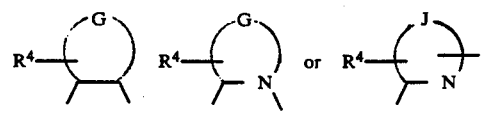

where G is a 3 to 7, preferably 3 or 4, membered chain of carbon atoms and optionally a nitrogen, oxygen or sulphur atom, preferably a propylene or butylene chain, J is a 2 to 5, preferably 2 or 3, membered chain of carbon atoms and optionally a nitrogen, oxygen or sulphur atom, preferably an ethylene, propylene or 2-oxa-propylene chain.

Especially prefered chelants for use according to the invention include those of formulae Id to Ii

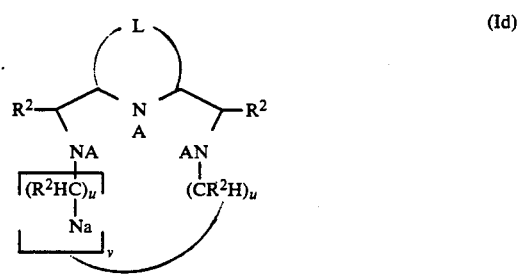 (Id)

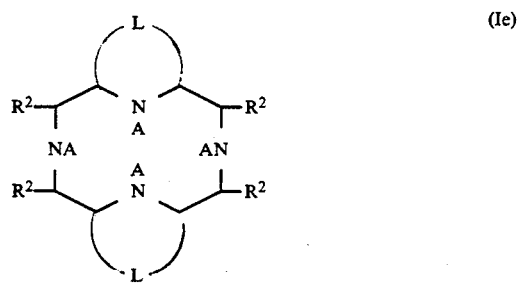 (Ie)

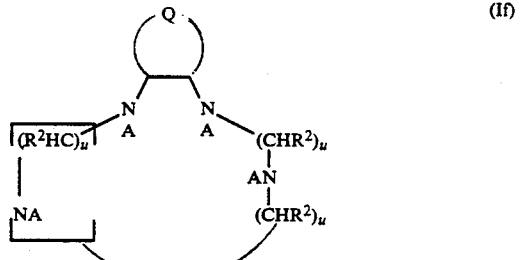 (If)

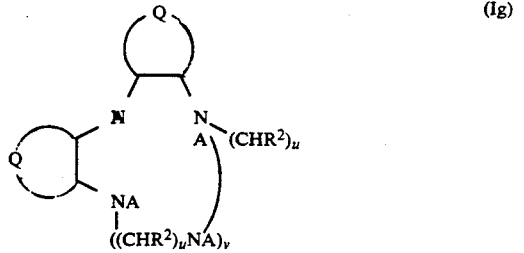 (Ig)

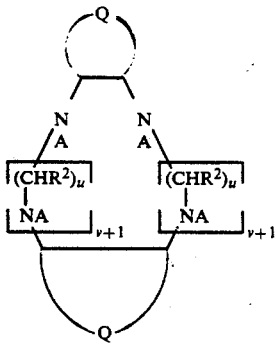
(Ih)

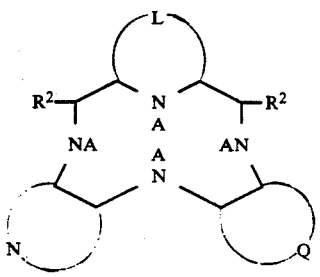
(Ii)

where
L is $(CHR^4)_2$, $(CHR^4)_3$ or $CHR^4OCHR^4$,
Q is $(CHR^4)_3$ or $(CHR^4)_4$,
u is 2 or 3,
and v is zero or 1.

Where a group $NR_2^2$ in a compound according to the invention is a nitrogen attached heterocyclic ring, it will conveniently be of formula

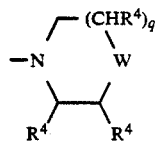

where q is 0,1 or 2, and W is $CHR^4$, $NR^4$, O or S, where q is zero W preferably being $CHR^4$. Particularly preferably such groups are of formula

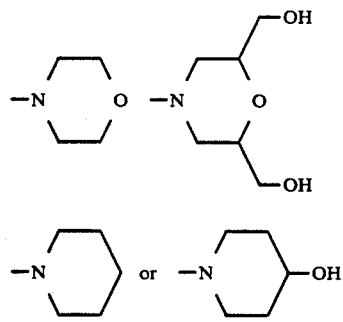

In the compounds of formula I, the groups Y preferably represent carboxylic acid or amide groups, for example groups of formula COOH, $CONH_2$, $CONCHR^4CHR^4W(CHR^4)_qCHR^4$, $CONHR^{2''}$ or $CONR_2^{2''}$ (where $R^{2''}$ is an alkyl or mono or poly hydroxyalkyl group, for example a $C_{1-6}$ alkyl group optionally carrying 1, 2, 3 or 4 hydroxyl groups).

Where Y is a carboxyl group, the compounds of formula I can conveniently form salts or chelates in which Y represents —COOM (wherein $M^+$ is a monovalent cation or a fraction of a polyvalent cation, for example an ammonium or substituted ammonium ion or a metal ion, for example an alkali metal or alkaline earth metal ion). Particularly preferably, $M^+$ is a cation deriving from an organic base, for example meglumine or lysine. In such salts or chelates one or more (but not necessarily all) of the carboxyl groups are transformed into COOM groups.

It is particularly preferred that the number of the ion-forming groups Y in the compounds of formula I be chosen to equal the valency of the metal species to be chelated by the compound formula I. Thus, for example, where Gd(III) is to be chelated, the compound of formula I (or salt thereof) preferably contains three ion-forming Y groups, for example —COOH (or —COOM). In this way, the metal chelate will be formed as a neutral species, a form preferred since the osmolalities in concentrated solutions of such compounds are low and since their toxicities relative to their ionic analogues are significantly reduced.

Compounds of formula I in which all the Y groups are —COOH groups or salts or amides of such compounds are especially preferred since compositions containing metal chelates of such compounds can readily be sterilized, for example by autoclaving.

Included amongst the particularly preferred compounds according to the invention are those of formulae Ib to Ii wherein each $R^2$ other than those forming fused rings represents a hydrogen atom or a mono- or polyhydroxylated alkyl group, Y represents a group of formula COZ and Z represents a hydroxyl group or a group $NHR^2$ and metal chelates and salt thereof.

Especially preferred compounds according to the invention include those of the following formulae Ij to Iaa

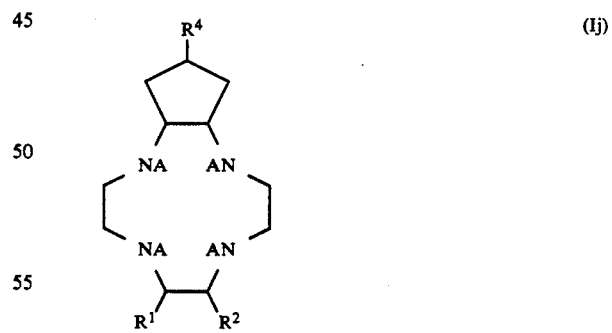
(Ij)

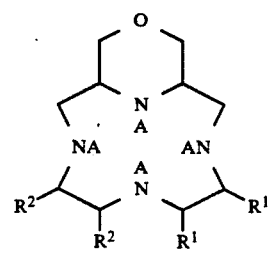
(Ik)

-continued
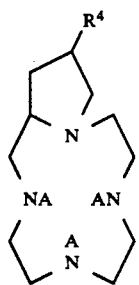
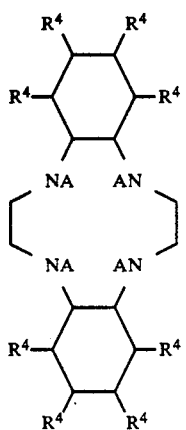
(Il)
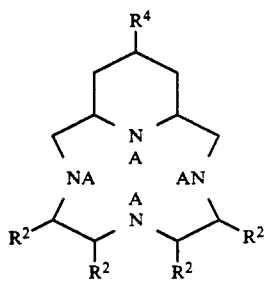
(Im)
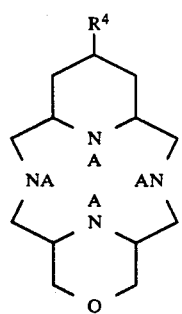
(In)
(Io)
(Ip)
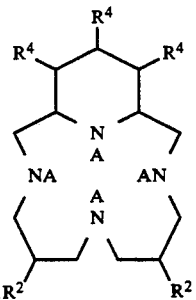
(Iq)
(Ir)
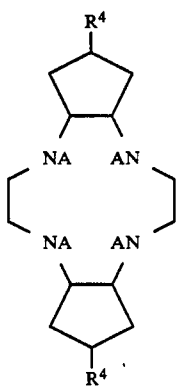
(Is)
(It)

-continued

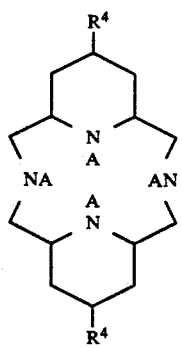
(Iu)

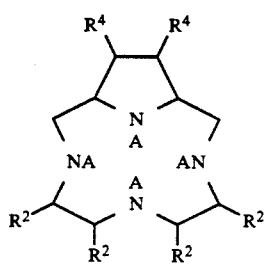
(Iv)

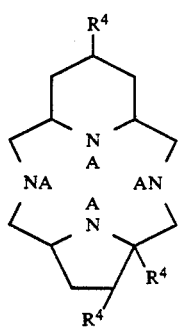
(Iw)

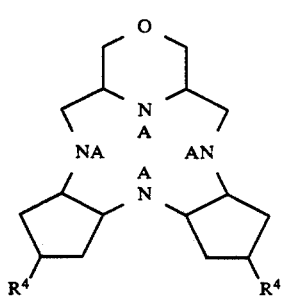
(Ix)

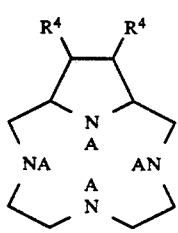
(Iy)

-continued

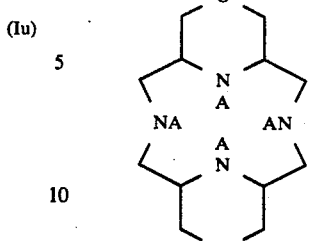
(Iz)

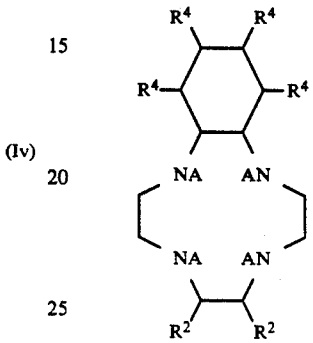
(IIaa)

preferably where all or all but one group A is a $CH_2Y$ group and/or where at least one group A is a non-ionizing hydrophilic group, and where some or all of the $R^2$ and $R^4$ groups are hydrophilic groups, preferably for $R^2$ hydroxy- or alkoxy-alkyl groups and for $R^4$ hydroxyl or hydroxy- or alkoxy- alkyl groups, especially where each A is hydrogen, hydroxypropyl, $CH_2COOH$, $CH_2CON(CH_3)$—$CH_2CHOHCH_2OH$, or $CH_2CONHR^7$ (where $R^7$ represents $CH_3$, $CH_2CHOHCH_2OH$ or $CH(CH_2OH)_2$ or a group —$CH_2CONCH_2CHR^{4''}W(CHR^{4''})_qCH_2$ where W represents an oxygen atom or a group $CH_2$ or CHOH, q is 0 or 1 and $R^{4''}$ is hydrogen or where q is 1 and W is oxygen each $R^{4''}$ may also represent a $C_{1-4}$ hydroxyalkyl group) and the metal chelates and the salts thereof.

Viewed from a further aspect, the invention also provides a process for the preparation of the compounds of the invention, said process comprising one or more of the following steps:

(a) reacting a compound of formula II

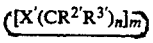 (II)

(where $R^{2'}$ and $R^{3'}$ are as defined for $R^2$ and $R^3$ or are protected $R^2$ or $R^3$ groups, and X' is a group X or a protected group X with the proviso that at least one X' group is of formula NH or $(CR^{2'}R^{3'})_pNH_2$) with a compound of formula III Lv-$(CR^{2'}R^{3'})_p$-Y' (III)

(where Y' is a group Y or $R^4$ or a protected group Y or $R^4$, $R^{2'}$ $R^{3'}$ are as hereinbefore defined and Lv is a leaving group for example a halogen atom, e.g. bromine or chlorine or a tosylate group and p is as hereinbefore defined) and if necessary subsequently removing any protecting groups used; and (b) converting a compound of formula I into a chelate complex or salt thereof.

The compounds of formula II may be prepared in a number of ways using techniques known from the literature or analogous to literature described techniques. In particular, starting materials as described in British Patent Application No. 8900719.9 may be used.

Thus for example such compounds may be prepared by condensing bifunctional compounds of formula IV

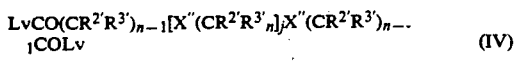

(where $R^{2'}$ and $R^{3'}$ are as defined above, Lv is as defined above or is an alkoxy leaving group j is 0 to m−3, and mid-chain X″ groups, if any, are groups X′ and end of chain X″ groups are oxygen, sulphur or ring nitrogen atoms or, preferably, NH groups) with a linking molecule of formula V

(where i is 1 to m−2 and $R^{2'}$, $R^{3'}$ and X″ are as hereinbefore defined) followed if necessary by removal of any protecting groups and if necessary by reduction.

The compounds of formula II may also be prepared by activating starting compounds of formula V, e.g. by tosylation, and condensing the product with a bifunctional compound of formula VI

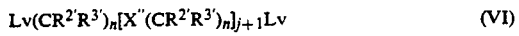

followed by removal of the tosyl and other protecting groups.

The compounds of formula II may also be prepared by cyclizing a linear compound of formula VII

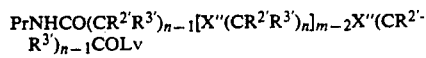

(where $R^{2'}$, $R^{3'}$ and X″ are as defined above but where ($CR^{2'}R^{3'}$) moieties adjacent X″ groups may represent carbonyl groups, Lv is a leaving group as defined above or is a hydroxyl group and Pr is a hydrogen atom or an amine protecting group) by reduction, tosylation and base-catalysed cyclization or by carboxyl activation cyclization followed by reduction.

Where this procedure is followed, and where a polypeptide of formula VII is used, selection of the amino acid precursors, e.g. use of hydroxy-proline, enables a bicyclo compound of formula II to be produced. Compounds of formula II may also be prepared by cyclization of macrocyclic compounds of formula VIII to produce the fused ring.

(where one X″ is a NH group and one $R^{2'}$ is a group condensable therewith, i.e. it carries a leaving group Lv, or where two $R^{2'}$ groups are condensable, e.g. one carries a leaving group and the other carries a displacing group and the other groups, X″, $R^{2'}$ and $R^{3'}$ are as hereinbefore defined).

The compounds of formula II can also be prepared by reduction of cyclic imines of formula XIX

(wherein X″, $R^{2'}$ and $R^{3'}$ are as defined above but wherein a [X″($CR^{2'}R^{3'}$)$_n$]$_2$X″ moiety represents an aromatic heterocyclic ring with two carbon attached —$CR^{3'}$=N— groups)

Thus for example compounds of formula II can be prepared using the following reaction schemes.

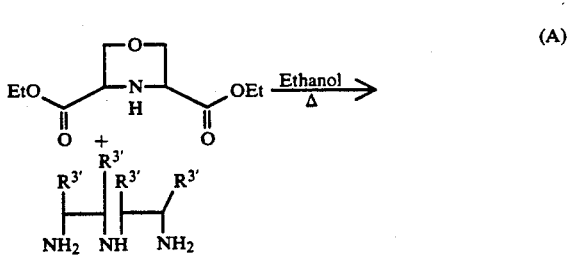

(A)

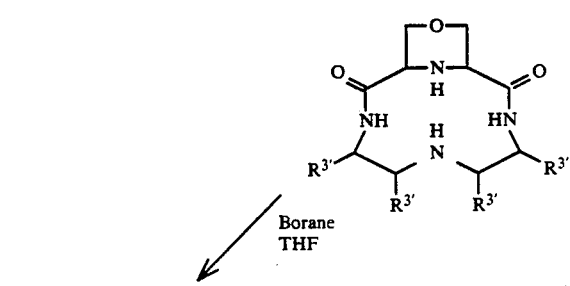

This is similar to the procedure by Tabushi et al. in Tetrahedron Letters 4339(1976) and 1049 (1977). In some cases the use of metal ions such as Ni$^{2+}$, K$^+$ or Na$^+$ as templates in the cyclization step may catalyse the reaction or improve the yield.

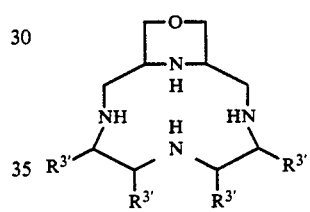

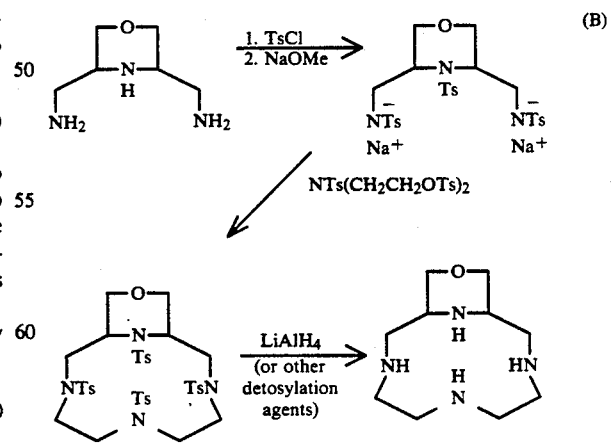

(B)

This is similar to the traditional cyclization procedure of Richmann et al. JACS 96:2268 (1974).

(C)

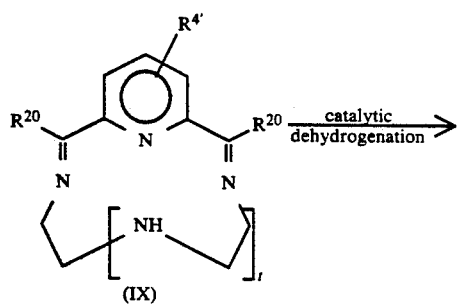

(IX)

t = 1, 2

R²⁰ = R³' e.g. H, CH₃

The compounds of formula IX can be prepared from dicarbonyl derivatives in a Schiff's base condensation as described by Nelson in Pure and Applied Chemistry 52:461–476 (1980), e.g.

(D)

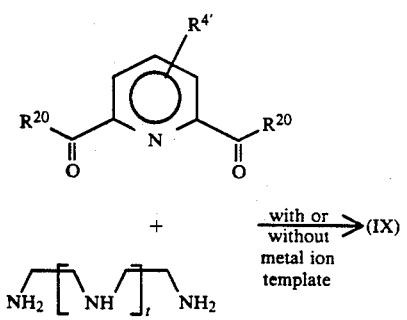

-continued

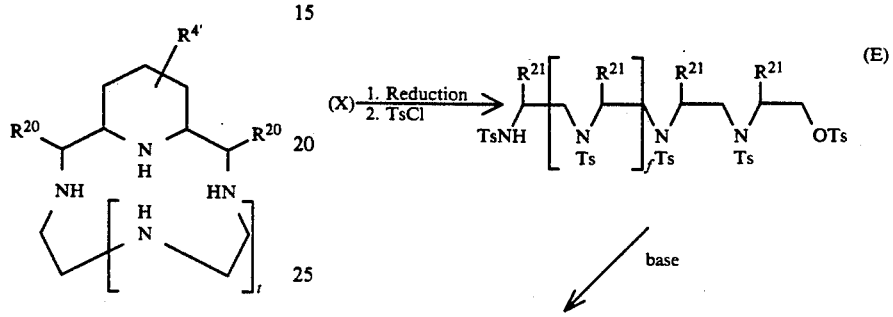

R²¹ = H, R²', R³' or an amino acid residue
f = 0 to 5

These are similar to the procedure of Moi et al. JACS 110: 6266 (1988).

Where one R²¹ on the polypeptide of formula X results from use of hydroxy proline, the resulting compound of formula (XI) carries a fused group

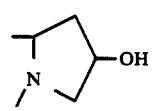

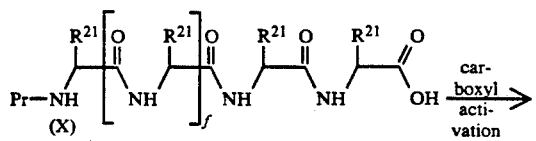

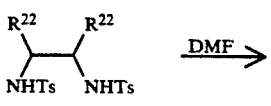

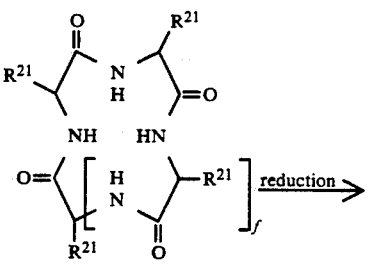

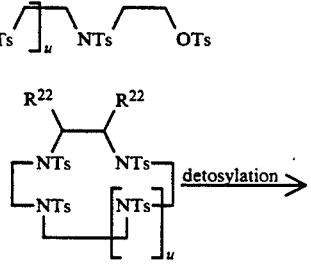

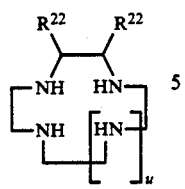

(where R²² is R²', R³' or is a ring, e.g. a 5 or 6 membered optionally hydrophilically substituted ring).

Reactions of this nature are described by Guerbet in EP-A-287465.

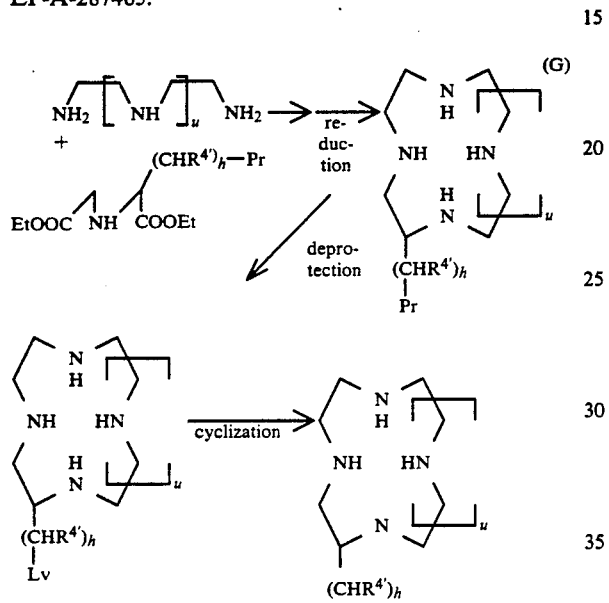

(where h is 3 or 4)

Further reaction schemes for the production of compounds of formula II will be evident to the skilled chemist from the literature, e.g. Tabushi et al. Tetr. Lett. 4339 (1976) and 1049 (1977), Richmann et al. JACS 96: 2268 (1974), Nelson, pure and Applied Chemistry 52: 461–476 (1980). Moi et al. JACS 110: 6266 (1988), EP-A-287465 (Guerbet) Stetter et al. Tetrahedron 37: 767 (1981), EP- A-232751 (Squibb), Hancock et al. JACS 110: 2788–2794 (1988), Smith et al. JACS 111: 7437–7443 (1989) and the references listed therein.

To introduce a $(CR^2R^3)_pY$ group onto a compound of formula II using the procedure of step (a) may be effected in an aqueous, preferably basic medium, for example by using a halocarboxylic acid Hal $(CR^{2'}R^{3'})_p$COOH or a metal, e.g. Li, salt thereof (where Hal is bromine or chlorine) followed by amidation or esterification of the carboxyl group.

The introduction of $(CR^2R^3)_pY$ or $(CR^2R^3)_pR^4$ moiety other than a carboxylic acid residue may for example be performed as follows:

a) To introduce a phosphonic acid moiety, the general method for synthesis of alpha-aminophosphonic acids described by K. Moedritzer et al. in J. Org. Chem 31: 1603 (1966) may be used.

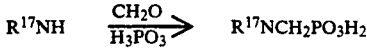

(XIII)　　　　　(XIV)

(of formula II)　　(of formula I)

(where $R^{17}NCH_2Y$ is a compound of formula I).

b) To introduce a hydroxamic acid moiety, the general method for transformation of an activated acid derivative into hydroxamic acid described by P. N. Turowski et al. in Inorg. Chem. 27: 474 (1988) may be used.

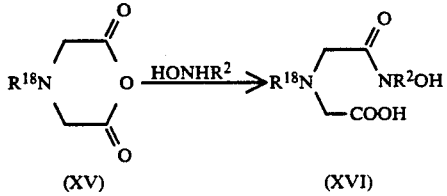

(XV)　　　　　(XVI)

(where $R^{18}N(CH_2COOH)CH_2Y$ is a compound of formula I).

c) To introduce a sulfonic acid moiety, synthesis may be performed by alkylation of an amino function for example with iodomethanesulfonic acid

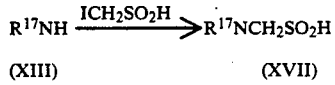

(XIII)　　　　　(XVII)

d) To introduce a nonionizing $(CR^2R^3)_pR^4$ group, synthesis may be performed by alkylation of an amino function with an optionally hydroxyl-protected alkyl (or alkoxyalkyl, hydroxyalkyl etc) halide:

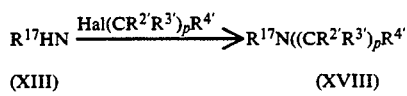

(XIII)　　　　　(XVIII)

followed if necessary by deprotection, e.g. debenzylation.

Amide derivatives of formula I may be produced from the oligo acids by methods analogous to those of EP-A-250358 or of EP-A-299795. Furthermore hydrophilic substituents on the skeleton of the chelants of formula I may be introduced by methods analogous to those of EP-A-299795.

Chelants of formula I may be used as the basis for bifunctional chelants or for polychelant compounds, that is compounds containing several independant chelant groups, by substituting for one Y or $R^1$ to $R^4$ group a bond or linkage to a macromolecule or polymer, e.g. a tissue specific biomolecule or a backbone polymer such as polylysine or polyethyleneimine which may carry several chelant groups and may itself be attached to a macromolecule to produce a bifunctional-polychelant. Such macromolecular derivatives of the compounds of formula I and the metal chelates and salts thereof form a further aspect of the present invention.

The linkage of a compound of formula I to a macromolecule or backbone polymer may be effected by any of the conventional methods such as the carbodiimide method, the mixed anhydride procedure of Krejcarek et al. (see Biochemical and Biophysical Research Communications 77: 581 (1977)), the cyclic anhydride method of Hnatowich et al. (see Science 220: 613 (1983) and elsewhere), the backbone conjugation techniques of Meares et al. (see Anal. Biochem. 142: 68 (1984) and elsewhere) and Schering (see EP-A-331616 for example) and by the use of linker molecules as described for example by Nycomed in WO-A-89/06979.

Salt and chelate formation may be performed in a conventional manner. The chelating agents of the formula I (as defined above but with the deletion of the second proviso) are particularly suitable for use in detoxification or in the formation of metal chelates, chelates which may be used for example in or as contrast agents for in vivo or in vitro magnetic resonance (MR), X-ray or ultrasound diagnostics (e.g. MR imaging and MR spectroscopy), or scintigraphy in or as therapeutic agents for radiotherapy, and such uses of these metal chelates form a further aspect of the present invention.

Salts or chelate complexes of the compounds of the invention containing a heavy metal atom or ion are particularly useful in diagnostic imaging or therapy. Especially preferred are salts or complexes with metals of atomic numbers 20-32, 42-44, 49 and 57 to 83, especially Gd, Dy and Yb. For use as an MR-diagnostics contrast agent, the chelated metal species is particularly suitably a paramagnetic species, the metal conveniently being a transition metal or a lanthanide, preferably having an atomic number of 21-29, 42, 44 or 57-71. Metal chelates in which the metal species is Eu, Gd, Dy, Ho, Cr, Mn or Fe are especially preferred and $Gd^{3+}$, $Mn^{2+}$ and $Dy^{3+}$ are particularly preferred. Chelates of ions of these metals specifically listed above with chelants of formula I (defined as above with the exclusion of the second proviso) or their salts with physiologically tolerable counterions are particularly useful for the diagnostic imaging procedures mentioned herein and they and their use are deemed to fall within the scope of the invention and references to chelates of compounds of formula I herein are consequently to be taken to include such chelates.

For use as contrast agents in MRI, the paramagnetic metal species is conveniently non-radioactive as radioactivity is a characteristic which is neither required nor desirable for MR-diagnostics contrast agents. For use as X-ray or ultrasound contrast agents, the chelated metal species is preferably a heavy metal species, for example a non-radioactive metal with an atomic number greater than 37, preferably greater than 50, e.g. $Dy^{3+}$. For use in scintigraphy and radiotherapy, the chelated metal species must of course be radioactive and any conventional complexable radioactive metal isotope, such as $^{99m}Tc$ or $^{111}In$ for example, may be used. For radiotherapy, the chelating agent may be in the form of a metal chelate with for example $^{153}Sm$, $^{67}Cu$ or $^{90}Y$.

For use in detoxification of heavy metals, the chelating agent must be in salt form with a physiologically acceptable counterion, e.g. sodium, calcium, ammonium, zinc or meglumine, e.g. as the sodium salt of the chelate of the compound of formula I with zinc or calcium.

Where the metal chelate carries an overall charge, such as is the case with the prior art Gd DTPA, it will conveniently be used in the form of a salt with a physiologically acceptable counterion, for example an ammonium, substituted ammonium, alkali metal or alkaline earth metal (e.g. calcium) cation or an anion deriving from an inorganic or organic acid. In this regard, meglumine salts are particularly preferred.

Viewed from a further aspect, the present invention provides a diagnostic or therapeutic agent comprising a metal chelate, whereof the chelating entity is the residue of a compound according to the present invention, together with at least one pharmaceutical or veterinary carrier or excipient, or adapted for formulation therewith or for inclusion in a pharmaceutical formulation for human or veterinary use.

Viewed from another aspect, the present invention provides a detoxification agent comprising a chelating agent according to the invention in the form of a weak complex or salt with a physiologically acceptable counterion, together with at least one pharmaceutical or veterinary carrier or excipient, or adapted for formulation therewith or for inclusion in a pharmaceutical formulation for human or veterinary use.

The diagnostic and therapeutic agents of the present invention may be formulated with conventional pharmaceutical or veterinary formulation aids, for example stablizers, antioxidants, osmolality adjusting agents, buffers, pH adjusting agents, etc. and may be in a form suitable for parenteral or enteral administration, for example injection or infusion or administration directly into a body cavity having an external escape duct, for example the gastrointestinal tract, the bladder or the uterus. Thus the agent of the present invention may be in a conventional pharmaceutical administration form such as a tablet, capsule, powder, solution, suspension, dispersion, syrup, suppository, etc; however, solutions, suspensions and dispersions in physiologically acceptable carrier media, for example water for injections, will generally be preferred.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (as for example, tromethamine hydrochloride), additions (e.g., 0.01 to 10 mole percent) of chelants (such as, for example, DTPA, DTPA-bisamide or non-complexed chelants of formula I) or calcium chelate complexes (as for example calcium DTPA, Ca-NaDTPA-bisamide, calcium salts or chelates of chelants of formula I), or, optionally, additions (e.g., 1 to 50 mole percent) of calcium of sodium salts (for example, calcium chloride, calcium ascorbate, calcium gluconate or calcium lactate combined with metal chelate complexes of chelants formula I and the like).

If the compounds are to be formulated in suspension form, e.g., in water or physiological saline for oral administration, a small amount of soluble chelate may be mixed with one or more of the inactive ingredients traditionally present in oral solutions and/or surfactants and/or aromatics for flavouring.

For MRI and for X-ray imaging of some portions of the body the most preferred mode for administering metal chelates as contrast agents is parentral, e.g., intravenous administration. Parenterally administrable forms, e.g., intravenous solutions, should be sterile and free from physiologically unacceptable agents, and should have low osmolality to minimize irritation of other adverse effects upon administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the chelates and which will not interfere with the manufacture, storage or use of products.

Where the diagnostic or therapeutic agent comprises a chelate or salt of a toxic metal species, e.g. a heavy metal ion, it may be desirable to include within the formulation a slight excess of the chelating agent, e.g. as discussed by Schering in DE-A-3640708, or more preferably a slight excess of the calcium salt of such a chelating agent. For MR-diagnostic examination, the diagnostic agent of the present invention, if in solution, suspension or dispersion form, will generally contain the metal chelate at concentration in the range 1 micromole to 1.5 mole per liter, preferably 0.1 to 700 mM. The diagnostic agent may however be supplied in a more concentrated form for dilution prior to administration. The diagnostic agent of the invention may conveniently be administered in amounts of from $10^{-3}$ to 3 mmol of the metal species per kilogram of body weight, e.g. about 1 mmol Dy/kg bodyweight.

For X-ray examination, the dose of the contrast agent should generally be higher and for scintigraphic examination the dose should generally be lower than for MR examination. For radiotherapy and detoxification, conventional dosages may be used.

Viewed from a further aspect, he present invention provides a method of generating enhanced images of the human or non-human animal body, which method comprises administering to said body a diagnostic agent according to the present invention and generating an X-ray, MR, ultrasound or scintigraphic image of at least a part of said body.

Viewed from a further aspect, the present invention provides a method of radiotherapy practised on the human or non-human animal body, which method comprises administering to said body a chelate of a radioactive metal species with a chelating agent according to the invention.

Viewed from a further aspect, the present invention provides a method of heavy metal detoxification practised on the human or non-human animal body, which method comprises administering to said body a chelating agent according to the invention in the form of its weak complex or salt with a physiologically acceptable counterion.

Viewed from a yet further aspect, the present invention also provides the use of the compounds, especially the metal chelates, according to the invention for the manufacture of diagnostic or therapeutic agents for use in methods of image generation, detoxification or radiotherapy practised on the human or non-human animal body.

Viewed from a still further aspect, the present invention provides a process for the preparation of the metal chelates of the invention which process comprises admixing in a solvent a compound of formula I or a salt (e.g. the sodium salt) or chelate thereof together with an at least sparingly soluble compound of said metal, for example a chloride, oxide, acetate or carbonate.

Viewed from a yet still further aspect, the present invention provides a process for the preparation of the diagnostic or therapeutic agent of the present invention, which comprises admixing a metal chelate according to the invention, or a physiologically acceptable salt thereof, together with at least one pharmaceutical or veterinary carrier or excipient.

Viewed from a yet still further aspect, the present invention provides a process for the preparation of the detoxification agent of the invention, which comprises admixing a chelating agent according to the invention in the form of a salt with a physiologically acceptable counterion together with at least one pharmaceutical or veterinary carrier or excipient.

The disclosures of all of the documents mentioned herein are incorporated by reference.

The present invention will now be illustrated further by the following non-limiting Examples. All ratios and percentages given herein are by weight and all temperatures are in degrees Celsius unless otherwise indicated.

EXAMPLE 1

13-Oxa-3,6,9,15-tetrakis(carboxymethyl)-3,6,9,15-tetraazabicyclo[9.3.1]pentadecane([12]N$_4$O$_4$(morph))

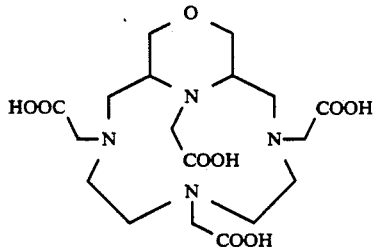

Route (A)

a) 4,8-Dioxo-13-oxa-3,6,9,15-tetraazabicyclo[9.3.1]-pentadecane([12]-dioxo-N$_4$(morph))

Iminodiacetic acid diethylester (10 mmol) and 2,6-bis-aminomethyl-morpholine (10 mmol) (described in British patent aplication no. 89 00719.9) are dissolved in ethanol and refluxed for 6 days. After stripping to dryness, the resulting oil is chromatogrphed on a silica column.

b) 13-Oxa-3,6,9,15-tetraazabicyclo[9.3.1]pentadecane ([12]N$_4$(morph))

The product from a) is disolved in 1M borane in THF (15 equiv.) at 0° C. and stirred for 1 hour. The solution is refluxed overnight, cooled and excess methanol is added. The reaction mixture is stripped and treated with a mixture of methanol and 6M HCl at ambient temperature. After evaporation of methanol, the pH of the solution is adjusted to 12 with NaOH, the reaction mixture is washed several times with chloroform and the organic phase evaporated to dryness. Alternatively the alkaline water phase is stripped to dryness, the residue dried by repeated evaporation of ethanol and the title compound extracted from the residue with dry ethanol. The resulting oil is purified on a silica column to yield the title compound.

c) 13-Oxa-3,6,9,15-tetrakis(carboxymethyl)-3,6,9,15-tetraazabicyclo[9.3.1]pentadecane([12]N₄O₃(morph))

The product from b) is treated with bromoacetic acid lithium salt (5 equiv.) in water while the pH is kept between 9 and 11 with LiOH and the temperature is gradually increased to 80° C. After reaction overnight, cooling and adjustment of pH to 3, the reaction mixture is treated with a strong cation exchanger. The product is separated from the resin by treatment with saturated ammonia in water. The mixture is stripped to dryness to yield the title compound The product is purified by precipitation at pH 3-3.5 in water/alcohol, or by reversed phase chromatography.

Route (B)

d) 13-Oxa-3,6,9,15-tetrakis(tert.-butoxycarbonylmethyl)-3,6,9,15-tetraazabicyclo[9.3.1]pentadecane

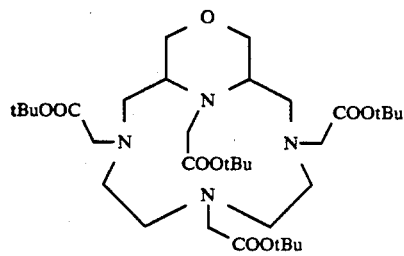

13-Oxa-3,6,9,15-tetraazabicyclo[9.3.1]pentadecane (0.5 g; 2.3 mmol) was dissolved in dry DMF. Potassium carbonate (1.6 g; 11.5 mmol) and tert-butyl bromoacetate (2.3 g; 11.5 mmol) were added and the reaction mixture was stirred at 50° C. overnight. The reaction mixture was cooled, evaporated to dryness, the residue was dissolved in chloroform (100 ml), washed with water (3×50 ml) and dried (MgSO₄). The chloroform was removed and the crude title compound purified by flash chromatography (SiO₂; eluent chloroform:methanol 9:1). Yield: 0.5 g; 32%. FAB MS: 671 (M+1).

f) 13-Oxa-3,6,9,15-tetrakis(carboxymethyl)-3,6,9,15-tetraazabicyclo[9.3.1]pentadecane

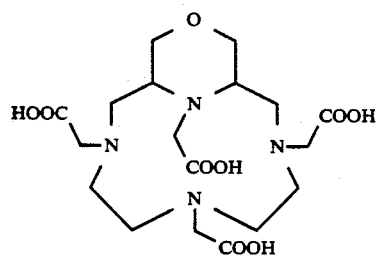

13-Oxa-3,6,9,15-tetrakis(tert.-butoxycarbonylmethyl)-3,6,9,15-tetraazabicyclo[9.3.1]pentadecane (0.4 g; 0.6 mmol) was dissolved in dichloromethane (3 ml) and trifluoroacetic acid (3 ml) was added. The reaction mixture was stirred at ambient temperature overnight, concentrated and treated with diethyl either to give the title compound in quantitative yield. FAB MS: 447 (M+1).

EXAMPLE 2

13-Hydroxy-4,8-bis(hydroxymethyl)-3,6,9,15-tetrakis(carboxymethyl)-3,6,9,15-tetraazabicyclo[9.3.1]pentadecane([12]Dihydroxymethyl-N₄O₃ (hydroxypip))

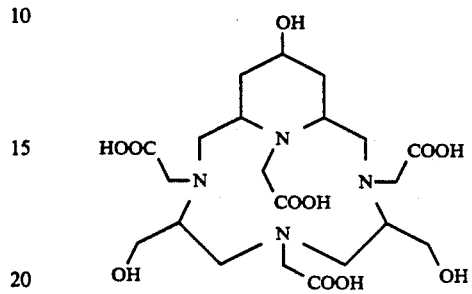

Route (A)

a) 2,10-Dioxo-4,8-bis(benzyloxymethyl)-13-hydroxy-3,6,9,15-tetraazabicyclo[9.3.1]pentadecane ([12]Dibenzyloxymethyl-dioxo-N₄(hydroxypip))

2,6-Bis(benzyloxymethyl)-1,4,7-triazaheptane (10 mmol), (described in WO-A-89/00557, Example 6 d) and 2,6-bis(ethyloxycarbonyl)-4-hydroxy-piperidine (10 mmol) (described in WO-A-90/08138)is reacted as described in Example 1 a) to yield the title compound.

b) 4,8-Bis(benzyloxymethyl)-13-hydroxy-3,6,9,15-tetraazabicyclo[9.3.1]pentadecane([12]Dibenzyloxymethyl-N₄(hydroxypip))

The product from a) is reduced with borane as described in Example 1 b) to yield the title compound.

c) 4,8-Bis(hydroxymethyl)-13-hydroxy-3,6,9,15-tetraazabicyclo[9.3.1]pentadecane ([12]Dihydroxymethyl-N₄(hydroxypip))

The product from b) is dissolved in methanol and treated with 10% palladium on carbon at 50° C. overnight. After filtration and evaporation, the title compound is purified on a silica column.

d) 13-Hydroxy-4,8-bis(hydroxymethyl)-3,6,9,15-tetrakis(carboxymethyl)-3,6,9,15-tetraazabicyclo [9.3.1]pentadecane([12]Dihydroxymethyl-N₄O₃(hydroxypip))

The product from c) is alkylated and purified as described in Example 1 c) to yield the title compound.

Route (B)

The title compound is prepared using a scheme analogous to that described in Example 1, Route B.

EXAMPLE 3

7-Hydroxy-15-oxa-3,11,17,18-tetrakis(carboxymethyl)-3,11,17,18-tetraazatricyclo[11.3.1.1.$^{5,9}$]octadecane

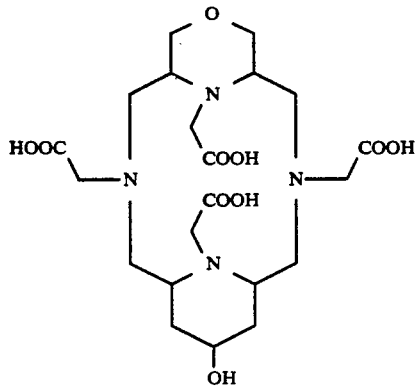

The title compound is prepared by the following reaction scheme:

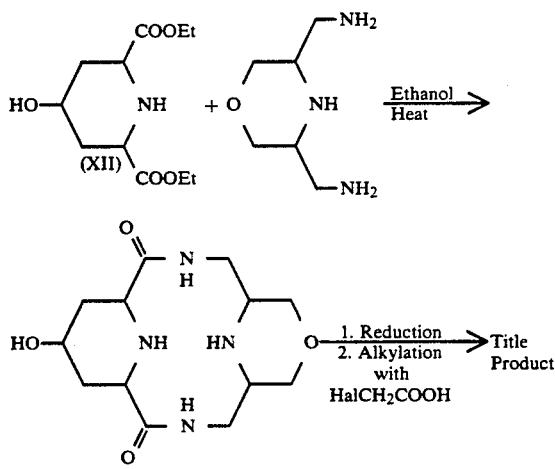

EXAMPLE 4

13-Oxa-3,6,9-tris(carboxymethyl)-3,6,9,15-tetraazabicyclo [9.3.1]pentadecane

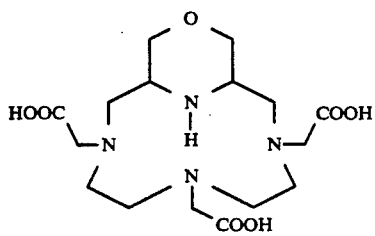

a) 4-Benzyl-3,5-bis(tosylamidomethyl)morpholine

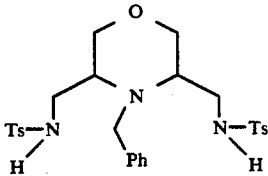

Tosyl chloride (5.5 g; 28 mmol) and triethylamine (2.9 g; 28 mmol) were dissolved in dry chloroform (100 ml) under nitrogen. 4-Benzyl-3,5-bis(aminomethyl)-morpholine (prepared according to WO-A-90/08138) (6.8 g; 28 mmol), dissolved in dry chloroform (100 ml), was added dropwise during 1 hour. The reaction mixture was stirred at ambient temperature overnight, washed with water (3×100 ml), dried (MgSO$_4$) and evaporated. The title compound was isolated after chromatography on SiO$_2$, using ethyl acetate as eluent. Yield: 10.6 g (70%). FAB MS: 544 (M+1).

b) 15-Benzyl-13-oxa-3,6,9-tris(tosyl)-3,6,9,15-tetraazabicyclo[9.3.1]pentadecane

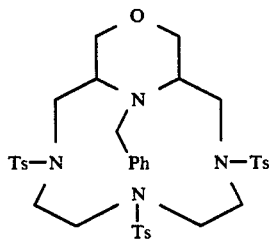

4 Benzyl-3,5-bis(tosylamidomethyl)-morpholine (2.3 g; 4.2 mmol) was dissolved in dry DMF (50 ml). Sodium hydride (50% in mineral oil, 1.1 g; 8.4 mmol) was added and the temperature raised to 100° C. after 30 min. O,N,O'-Tris(tosyl)-diethanolamine (made according to the procedure described in Can. J. Chemistry 45: 1555 (1967)) (2.4 g; 4.2 mmol) dissolved in dry DMF (100 ml), was added dropwise during 1 hour. The reaction mixture was stirred at 100° C. overnight, cooled on ice/water and 200 ml water was added dropwise. The precipitate was filtered off and dried. Yield: 8 g; 50%. FAB MS: 768 (M+1).

c) 13-Oxa-3,6,9,15-tetraazabicyclo[9.3.1]pentadecane

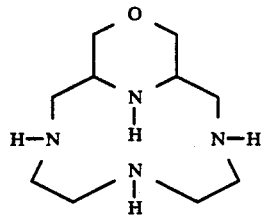

15 Benzyl-13-oxa-3,6,9-tris(tosyl)-3,6,9,15-tetraazabicyclo[9.3.1]pentadecane (2 g; 2.6 mmol) was dissolved in concentrated sulfuric acid (10 ml) and heated to 100° C. for 48 hours. The reaction mixture was cooled on ice/water and diethyl ether (30 ml) was added dropwise. The precipitated polyhydrosulfate salt was filtered under nitrogen, washed with small volumes of dry diethyl ether and dissolved in 50% sodium hydroxide solution. The resulting mixture was extracted continuously with chloroform for 48 hours. The chloroform was removed to yield the title compound. Yield: 0.23 g, 42%. FAB MS: 215 (M+1).

d) 13-Oxa-3,6,9-tris(tert.-butoxycarbonylmethyl)-3,6,9,15-tetraazabicyclo[9.3.1]pentadecane

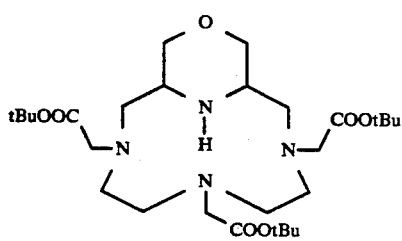

13-Oxa-3,6,9,15-tetraazabicyclo[9.3.1]pentadecane (0.3 g; 1.4 mmol) was dissolved in dry DMF. Sodium hydrogen carbonate (0.6 g; 7 mmol) and tert-butyl bromoacetate (1.4 g; 7 mmol) were added and the reaction mixture was stirred at ambient temperature overnight. The reaction mixture was evaporated to dryness, the residue was dissolved in chloroform (100 ml), washed with water (3×50 ml) and dried (MgSO₄). The chloroform was removed and the crude title compound purified by flash chromatography (SiO₂; eluent chloroform:methanol 9:1). Yield: 0.47 g; 60%. FAB MS: 557 (M+1).

e) 13-Oxa-3,6,9-tris(carboxymethyl)-3,6,9,15-tetraazabicyclo[9.3.1]pentadecane

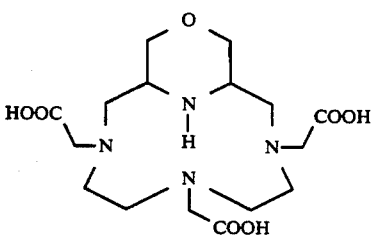

13-Oxa-3,6,9-tris(tert.-butoxycarbonylmethyl)-3,6,9,15-tetraazabicyclo[9.3.1]pentadecane (0.4 g; 0.7 mmol) was dissolved in dichloromethane (3 ml) and trifluoroacetic acid (3 ml) was added. The reaction mixture was stirred at ambient temperature overnight, concentrated and treated with diethyl ether to give the title compound in quantitative yield. FAB MS: 389 (M+1).

EXAMPLE 5

Gadolinium chelate of 13-oxa-3,6,9-tris(carboxymethyl)-3,6,9,15-tetraazabicyclo[9.3.1]pentadecane 13-Oxa-3,6,9-tris(carboxymethyl)-3,6,9,15-tetraazabicyclo[9.3.1]pentadecane (Example 4) (0.23 g; 0.6 mmol) was dissolved in water (2 ml) and the pH adjusted to 5 with 1M NaOH. Gadolinium oxide (0.11 g; 0.3 mmol) was added and the resulting mixture stirred at 90° C. for 24 hours. The reaction mixture was filtered and the filtrate evaporated to dryness to yield 0.3 g (92%) of a yellow solid. FAB MS: 543 (M+1).

EXAMPLE 6

15-(2'-Hydroxypropyl)-13-oxa-3,6,9-tris(carboxymethyl)-3,6,9,15-tetraazabicyclo[9.3.1]pentadecane

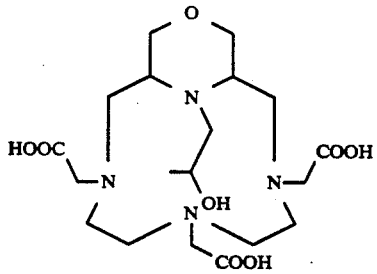

13-Oxa-3,6,9-tris(carboxymethyl)-3,6,9,15-tetraazabicyclo[9.3.1]pentadecane (Example 4) (0.23 g; 0.6 mmol) is dissolved in water (2 ml) and the pH adjusted to 12 with 1M NaOH. The solution is cooled to ambient temperature, and propylene oxide (0.05 g; 0.9 mmol) is added. The reaction flask is stoppered, and left to stir at ambient temperature overnight. The reaction mixture is acidified and treated with a cation exchange resin to give the title compound.

EXAMPLE 7

Sodium salt of the cadolinium chelate of 13-oxa-3,6,9,15-tetrakis(carboxymethyl)-3,6,9,15-tetraazabicyclo9.3.1]pentadecane 13-Oxa-3,6,9,15-tetrakis(carboxymethyl)-3,6,9,15-tetraazabicyclo[9.3.1]pentadecane (Example 1) (0.22 g; 0.5 mmol) was dissolved in water (2 ml) and the pH adjusted to 5 with 1M NaOH. Gadolinium oxide (0.09 g; 0.25 mmol) was added and the resulting mixture stirred at 90° C. for 24 hours. The reaction mixture was filtered and the filtrate evaporated to dryness to yield 0.3 g (92%) of a yellow solid. FAB MS: 622 (M+Na).

We claim:

1. A compound of formula Ik

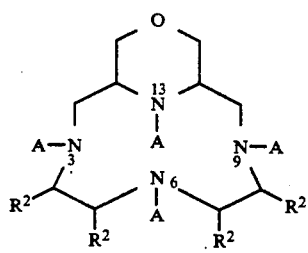

(Ik)

wherein
three groups A are independently groups of formula CH₂Y and the remaining A group represents a hydrogen atom, a C₁₋₃alkyl group optionally substituted by a group Y or, in the 15-position, a group R⁴;

each Y independently represents a group —COZ, —POZ₂ or —CON(OH)R²;

each Z independently represents a group —OR² or —NR²R²;

each R² independently represents a hydrogen atom or a C₁₋₈ alkyl group optionally mono- or poly-substituted or a pair of R² groups represent a bridging group which together with the intervening two carbon and one nitrogen atoms form a 5 to 8 membered saturated fused ring containing one nitrogen heteroatom and, where the ring is 6-membered, optionally one further ring heteroatom selected from nitrogen, oxygen and sulphur, said ring optionally being substituted by a group $R^4$; and each $R^4$ independently represents a hydroxy group or an optionally mono- or poly-hydroxylated and/or alkoxylated $C_{1-8}$alkyl group; or a chelate complex or salt thereof.

2. A compound as claimed in claim 1 being a compound of formula Ik wherein each $R^2$ is hydrogen and the A groups at the 3-, 6- and 9-positions are carboxymethyl groups, or a chelate complex or salt thereof.

3. A compound as claimed in claim 1 being a chelate complex of a compound of formula Ik with a paramagnetic metal or other heavy metal ion, or a salt thereof.

4. A compound as claimed in claim 2 being a chelate complex of a compound of formula Ik with a paramagnetic metal or other heavy metal ion, or a salt thereof.

5. A compound as claimed in claim 3 wherein said metal is selected from Eu, Gd, Dy, Ho, Cr, Mn and Fe.

6. A compound as claimed in claim 4 wherein said metal is selected from Eu, Gd, Dy, Ho, Cr, Mn and Fe.

7. A diagnostic or therapeutic composition comprising a metal chelate, whereof the chelating moiety is the residue of a compound of formula Ik as defined in claim 1, together with at least one pharmaceutical or veterinary carrier or excipient.

8. A method of generating enhanced images of the human or non-human animal body, which method comprises administering to said body a diagnostic agent as claimed in claim 7 and generating an X-ray, MR, ultrasound or scintigraphic image of at least a part of said body.

9. A compound of formula Ik

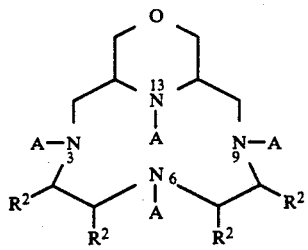

(Ik)

wherein
three groups A are independently groups of formula $CH_2Y$ and the remaining A group represents a hydrogen atom, a $C_{1-3}$alkyl group optionally substituted by a group Y or, in the 15-position, a group $R^4$;

each Y independently represents a group —COZ, —$POZ_2$ or —CON(OH)$R^2$;

each Z independently represents a group —$OR^2$ or —$NR^2R^2$;

each $R^2$ independently represents a hydrogen atom or a $C_{1-8}$ alkyl group optionally mono- or poly-substituted or a pair of $R^2$ groups represent a bridging group which together with the intervening two carbon and one nitrogen atoms form a 5 to 8 membered saturated fused ring containing one nitrogen heteroatom and, where the ring is 6-membered, optionally one further ring heteroatom selected from nitrogen, oxygen and sulphur, said ring optionally being substituted by a group $R^4$; and each $R^4$ independently represents a hydroxy group or an optionally mono- or poly-hydroxylated and/or alkoxylated $C_{1-8}$alkyl group.

* * * * *

UNITED STATES PATENT AND TRADEMARK OFFICE
CERTIFICATE OF CORRECTION

PATENT NO. : 5,322,681
DATED : June 21, 1994
INVENTOR(S) : Klaveness et al.

It is certified that error appears in the above-identified patent and that said Letters Patent is hereby corrected as shown below:

On the cover page, item [75]:

please add the following inventors:

--Pål Rongved, Hellvik, Norway
Arne Berg , Blommenholm, Norway--

Column 26, claim 8, in the structural formula Ik,
please delete "$N^{13}$" and insert --$N^{15}$--.

Column 27, claim 8, line 3, delete "agent" and insert --composition--.

Column 28, claim 9, in the structural formula Ik,
please delete "$N^{13}$" and insert --$N^{15}$--.

Signed and Sealed this

Twenty-second Day of November, 1994

Attest:

BRUCE LEHMAN

*Attesting Officer*    *Commissioner of Patents and Trademarks*